United States Patent [19]

Durant et al.

[11] 4,112,104

[45] Sep. 5, 1978

[54] PHARMACOLOGICALLY ACTIVE COMPOUNDS

[75] Inventors: Graham John Durant; Charon Robin Ganellin, both of Welwyn Garden City, England

[73] Assignee: Smith Kline & French Laboratories Limited, Welwyn Garden City, England

[21] Appl. No.: 770,340

[22] Filed: Feb. 22, 1977

Related U.S. Application Data

[60] Division of Ser. No. 640,525, Dec. 15, 1975, Pat. No. 4,025,527, which is a continuation-in-part of Ser. No. 481,716, Jun. 21, 1974, abandoned.

[30] Foreign Application Priority Data

Jul. 13, 1973 [GB] United Kingdom ............... 33428/73
Nov. 12, 1975 [GB] United Kingdom ............... 46732/75

[51] Int. Cl.$^2$ .................. A61K 31/425; A61K 31/42
[52] U.S. Cl. ..................................... 424/270; 424/272
[58] Field of Search ........... 260/302 R, 307 R, 302 H; 424/270, 272

[56] References Cited

U.S. PATENT DOCUMENTS 4,025,527  5/1977  Durant et al. ...................... 424/270

*Primary Examiner*—Paul M. Coughlan, Jr.
*Attorney, Agent, or Firm*—Joan S. Keps; Richard D. Foggio; William H. Edgerton

[57] ABSTRACT

The compounds are N,N'-substituted thioureas, ureas and guanidines which are H-2 histamine receptor inhibitors. Two compounds of this invention are N,N'-bis[2-((4-methyl-5-imidazolyl)methylthio)ethyl]thiourea and N,N'-bis]2-((4-methyl-5-imidazoly)methylthio)ethyl]-N'''-cyanoguanidine.

4 Claims, No Drawings

PHARMACOLOGICALLY ACTIVE COMPOUNDS

This is a division of application Ser. No. 640,525 filed Dec. 15, 1975, now U.S. Pat. No. 4,025,527 which is a continuation-in-part of Ser. No. 481,716 filed June 21, 1974, now abandoned.

This invention relates to pharmacologically active N,N'-substituted thioureas, ureas and guanidines. These compounds are inhibitors of H-2 histamine receptors. In addition, this invention relates to pharmaceutical compositions and methods of inhibiting H-2 histamine receptors with these compounds.

The compounds of the invention can exist as the addition salt but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has been described by Black et al. (Nature 1972, 236, 385) which are distinguished by the fact that they act at histamine receptors other than the H-1 receptor and these receptors have been designated as H-2 receptors. This latter group of substances, to certain of which the present invention relates, are thus of utility in inhibiting certain actions of histamine which are not inhibited by the above-mentioned "antihistamines", that is they are H-2 histamine receptor inhibitors. Inhibitors of H-2 histamine receptors, which are also referred to as histamine H-2 antagonists, are useful for example, as inhibitors of gastric acid secretion, as anti-inflammatory agents and as agents which act on the cardiovascular system, for example as inhibitors of the effects of histamine on blood pressure. The histamine H-2 antagonists of this invention may also be of utility as inhibitors of certain actions of gastrin. In the treatment of certain conditions, for example inflammation and in inhibiting the actions of histamine on blood pressure, a combination of histamine H-1 and H-2 antagonists is useful.

Throughout the present specification, by the term "lower alkyl" we mean an alkyl group containing from 1 to 4 carbon atoms.

The compounds with which the present invention is concerned may be represented by the following general formula:

$$Het_1-(CH_2)_{m_1}-Z_1-B_1-NHCNH-B_2-Z_2-(CH_2)_{m_2}-Het_2$$
$$\overset{X}{\underset{\|}{}}$$

wherein $Het_1$ and $Het_2$, which may be the same or different, are each a nitrogen containing 5 or 6 membered heterocyclic ring such as imidazole, pyridine, thiazole, isothiazole, oxazole, isoxazole, triazole or thiadiazole, which is optionally substituted by lower alkyl, hydroxyl, halogen or amino: $Z_1$ and $Z_2$ are sulphur or a methylene group: $B_1$ is $(CH_2)_{n_1}$ and $B_2$ is $(CH_2)_{n_2}$ and when $Z_1$ is sulphur and $m_1$ is 1, $B_1$ may also be $CH_2CHR$, $CHRCH_2$, $CHRCH_2CH_2$, $CH_2CHRCH_2$ or $CH_2CH_2CHR$ wherein R is methyl or ethyl or when $Z_1$ and $Z_2$ are sulphur and $m_1$ and $m_2$ are 1, both $B_1$ and $B_2$ may also be

$m_1$ and $m_2$ are 0, 1 or 2 and $n_1$ and $n_2$ are 2 or 3, provided that the sum of $m_1$ and $n_1$ and the sum of $m_2$ and $n_2$ are from 2 to 4; and X is sulphur, oxygen, or NY wherein Y is hydrogen, cyano, $CONH_2$ or $SO_2R_1$ wherein $R_1$ is lower alkyl or phenyl, provided that, when X is NH, at least one of $Z_1$ or $Z_2$ is sulphur, and that when X is NH the sum of $m_1$ and $n_1$ is 3 or 4 if $Het_1$ is imidazole and the sum of $m_2$ and $n_2$ is 3 or 4 if $Het_2$ is imidazole; or a pharmaceutically acceptable acid addition salt thereof.

It will be understood that the structure illustrated in Formula I is only one of several representations and that other tautomeric forms are also covered by the present invention.

A preferred group of compounds are those wherein $B_1$ is $(CH_2)_{n_1}$ and $B_2$ is $(CH_2)_{n_2}$ and within this group it is further preferred that $Het_1-(CH_2)_{m_1}-Z_1-B_1$ and $Het_2-(CH_2)_{m_2}-Z_2-B_2$ are the same. A further preference is for the sum of $m_1$ and $n_1$ and the sum of $m_2$ and $n_2$ to be 3 or 4 and particularly preferably, $m_1$ and $m_2$ are each 1 and $n_1$ and $n_2$ are each 2; compounds wherein $Z_1$ and $Z_2$ are sulphur are also preferred: it follows therefore that compounds wherein the N-substituents are $Het_1-CH_2S(CH_2)_2$ and $Het_2-CH_2S(CH_2)_2$ are an important part of the present invention. $Het_1$ and $Het_2$ may particularly usefully be imidazole, thiazole, isothiazole or pyridine optionally substituted by methyl, hydroxyl or halogen for example they may be 4-imidazolyl, 5-methyl-4-imidazolyl, 5-bromo-4-imidazolyl, 2-pyridyl, 3-methyl-2-pyridyl, 3-bromo-2-pyridyl, 3-chloro-2-pyridyl, 2-thiazolyl, 3-isothiazolyl, 4-chloro-3-isothiazolyl or 4-bromo-3-isothiazolyl. A useful series of histamine H-2 antagonist compounds are those wherein X is sulphur and, in a further useful series, X is NY and Y is hydrogen or cyano.

Examples of specific compounds having histamine H-2 antagonist activity which are within the scope of the present invention are:

N,N'-bis[2-((4-methyl-5-imidazolyl)methylthio)ethyl]-thiourea,

N,N'-bis[2-((4-methyl-5-imidazolyl)methylthio)ethyl]-N"cyanoguanidine,

N,N'-bis[2-((4-methyl-5-imidazolyl)methylthio)ethyl]-guanidine,

N,N'-bis[2-((2-thiazolyl)methylthio)ethyl]-N"-cyanoguanidine,

N-[2-((4-methyl-5-imidazolyl)methylthio)propyl]-N'-[2-((4-methyl-5-imidazolyl)methylthio)ethyl]guanidine and N,N'-bis[2-((4-methyl-5-imidazolyl)methylthio)propyl]-guanidine.

The compounds of the present invention wherein X is sulphur may be produced from an amine of the formula $Het_1-(CH_2)_{m_1}-Z_1-B_1-NH_2$, wherein $Het_1$, $m_1$, $Z_1$ and $B_1$ have the same significance as in Formula I, by reaction thereof with carbon disulphide and a lower alkyl halide or sulphate such as methyl iodide or methyl sulphate to give the corresponding dithiocarbamic ester of Formula II (which will of course normally exist in the form of the acid addition salt):

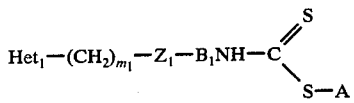

wherein A is lower alkyl and subsequent reaction of this compound under alkaline conditions (e.g. in the presence of sodium ethoxide in a solvent such as ethanol) with an amine of Formula $Het_2-(CH_2)_{m_2}-Z_2-B_2-NH_2$. Where $Het_1-(CH_2)_{m_1}-Z_1-B_1$ and $Het_2-(CH_2)_{m_2}-Z_2-B_2$ are the same, the required compounds can be produced without isolation of an intermediate of Formula II by the reaction of carbon disulphide with an excess (two moles or more) of the amine of Formula $Het_1-(CH_2)_{m_1}-Z_1-B_1-NH_2$, this reaction being conveniently carried out in a solvent such as ethanol.

Compounds of Formula I wherein X is N-Y may be produced, directly or indirectly, by reactions involving the use of a compound of Formula III:

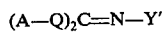 FORMULA III wherein Q is sulphur or oxygen, A is alkyl and Y' is cyano, benzoyl or $SO_2R_1$, $R_1$ having the same significance as in Formula I.

When the compound of Formula III is reacted with an equivalent amount of an amine of Formula $Het_1-(CH_2)_{m_1}-Z_1-B_1-NH_2$, the intermediate product of Formula IV:

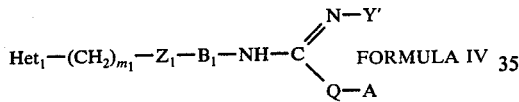 FORMULA IV is formed. This reaction may conveniently be carried out in a solvent such as ethanol at a temperature of from 20°-100° C. Reaction of this intermediate with the amine of Formula $Het_2-(CH_2)_{m_2}-Z_2-B_2-NH_2$, which reaction may also be carried out in a solvent or in the absence thereof yields a product of Formula V:

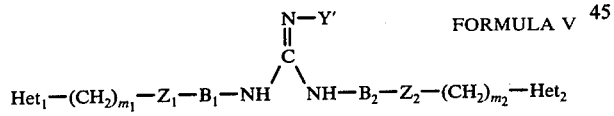 FORMULA V

The above mentioned second stage of the reaction may be modified by first adding to the intermediate of Formula V a silver salt such as silver nitrate, removing the silver methyl mercaptide which is formed, and then proceeding with the reaction with the amine $Het_2-(CH_2)_{m_2}-Z_2-B_2-NH_2$ to give the product of Formula V. Alternatively, when $Het_1-(CH_2)_{m_1}-Z_1-B_1-NH_2$ is the same as $Het_2-(CH_2)_{m_2}-Z_2-B_2-NH_2$, a single-stage reaction may be employed using an excess i.e. two moles or more of the amine formula $Het_1-(CH_2)_{m_1}-Z_1-B_1-NH_2$ for each mole of the compound of Formula III. In this case also the reaction is conveniently carried out in the absence of a solvent at an elevated temperature e.g., 80°-120° C., or in a solvent, e.g., in refluxing pyridine.

When, in Formula V, Y' is cyano or $SO_2R_1$ the compounds are of course within the scope of Formula I. Acid hydrolysis of the compounds of Formula V wherein Y' is benzoyl or cyano yields the compounds of Formula I wherein Y is hydrogen: mild acid hydrolysis of the compounds of Formula VI wherein Y' is cyano yields the compounds of Formula I wherein Y is $CONH_2$.

The compounds of Formula I wherein Y is cyano may alternatively be prepared from the compounds wherein X is sulphur by reaction of the latter with a heavy metal salt of cyanamide such as lead, mercury or cadmium cyanamide in a solvent such as acetonitrile and/or dimethylformamide.

An alternative method which may be used for the production of compounds of Formula I wherein Y is hydrogen commences from a thiourea of the Formula VI:

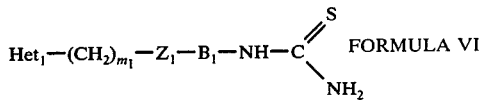 FORMULA VI

Reaction of this compound with a lower alkyl halide such as methyl iodide gives the isothiourea of Formula VII:

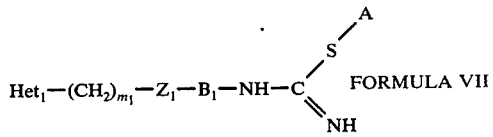 FORMULA VII wherein A is lower alkyl, and reaction of this isothiourea with an amine of Formula $Het_2-(CH_2)_{m_2}-Z_2-B_2-NH_2$ yields the required compound.

Compounds where X is oxygen and $Het_1-(CH_2)_{m_1}-Z_1-B_1-NH_2$ and $Het_2-(CH_2)_{m_2}-Z_2-B_2-NH_2$ are the same may be conveniently prepared by the reaction of the amine $Het_1-(CH_2)_{m_1}-Z_1-B_1-NH_2$ with carbonyl diimidazole e.g., by fusion at an elevated temperature, or by reflux in a solvent such as dimethylformamide.

The amines of Formulae $Het_1-(CH_2)_{m_1}-Z_1-B_1-NH_2$ and $Het_2-(CH_2)_{m_2}-Z_2-B_2-NH_2$ may be produced by the reaction of a compound of Formula X:

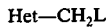 FORMULA X wherein Het has the same significance as $Het_1$ and $Het_2$ in Formula I and L is hydroxyl, halogen or methoxy, with an aminethiol of Formula XI:

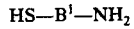 FORMULA XI wherein $B^1$ has the same significance as $B_1$ and $B_2$ in Formula I.

As stated above, the compounds represented by Formula I have been found to have pharmacological activity in the animal body as antagonists to certain actions of histamine which are not blocked by "anti-histamines" such as mepyramine. For example, they have been found to inhibit selectively the histamine-stimulated secretion of gastric acid from the perfused stomachs of rats anaesthetised with urethane at doses of from 0.5 to 256 micromoles per kilogram intravenously. Similarly, the action of these compounds is demonstrated by their antagonism to the effects of histamine on other tissues which, according to the above-mentioned paper of Black et al., are H-2receptors. Examples of such tissues are perfused isolated guinea-pig atrium and isolated rat uterus. These compounds of this invention have also been found to inhibit the secretion of gastric acid stimulated by pentagastrin or by food.

The level of activity found for the compounds of the present invention is illustrated by the effective dose range in the anaesthetised rat, as mentioned above of from 0.5 to 256 micromoles per kilogram, intravenously. Many of the compounds of the present invention produce a 50% inhibition in this test at a dose of from 1 to 10 micromoles per kilogram.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids and may conveniently be formed from the corresponding bases of Formula I by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula I or a pharmaceutically acceptable acid addition salt thereof and methods of inhibiting H-2 histamine receptors which comprise administering a compound of Formula I or a pharmaceutically acceptable acid addition salt thereof are also objects of this invention. The pharmaceutical carrier employed may be, for example, either a solid or liquid. Exemplary of solid carriers are lactose, terra alba, sucrose, talc, gelatin agar, pectin, acacia, magnesium stearate, stearic acid and the like. Examplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg. most preferably from about 100 mg. to about 200 mg.

The active ingredient will preferably be administered in equal doses one to three times per day. The daily dosage regimen will preferably be from about 150 mg. to about 750 mg. most preferably from about 300 mg. to about 600 mg.

Other pharmacologically active compounds may in certain cases be included in the composition. Advantageously the composition will be made up in a dosage unit form appropriate to the desired mode of administration, for example as a tablet, capsule or injectable solution.

The invention is illustrated but in no way limited by the following Examples:

EXAMPLE 1

N,N'bis-[2-((4-Methyl-5-imidazolyl)methylthio)ethyl]-thiourea (i) A solution of 4-methyl-5-((2-aminoethyl)thiomethyl)imidazole (10.2 g.) in ethanol (75 ml.) was added slowly, with stirring, to carbon disulphide (200 ml.). The mixture was set aside overnight at room temperature and the solid formed was collected and recrystallised from aqueous isopropyl alcohol to afford N-[2-((4-methyl-5-imidazolyl)methylthio)ethyl]dithiocarbamic acid (9.8 g.) m.p. 127°–129°.

(Found: C, 38.6; H, 5.5; N, 16.7% $C_8H_{13}N_3S_3$ requires: C, 38.8; H, 5.3; N, 17.0%)

(ii) Methyl iodide (4.0 g.) was added to a suspension of the dithiocarbamic acid (7.0 g.) in methanol (100 ml). After stirring at room temperature for 1.5 hours a solution was obtained. Concentration, followed by recrystallisation of the residue from isopropyl alcohol-ether gave S-methyl-N-[2-((4-methyl-5-imidazolyl)methylthio))ethyl]dithiocarbamate hydriodide (8.6 g.), m.p. 167°–169°.

(iii) A solution prepared from S-methyl-N-[2-((4-methyl-5-imidazolyl)methylthio))ethyl]dithiocarbamate hydriodide (15.6 g.), 4-methyl-5-((2-aminoethyl)thiomethyl)imidazole (6.8 g.) in ethanol (200 ml.) containing sodium (0.9 g.) was heated under reflux for 8 hours. Concentration followed by chromatographic purification of the product on a column of silica gel with ethyl acetate-isopropyl alcohol (5:1) as eluant gave the title compound which was converted to the dihydrochloride (2.5 g., m.p. 115°–120°) with ethanolic hydrogen chloride.

(Found: C, 39.1; H, 5.7; N, 17.8; S, 20.6; Cl, 15.3% $C_{15}H_{24}N_6S_3.2HCl$ requires: C, 39.4; H, 5.7; N, 18.4; S, 21.0; Cl, 15.5%)

(b) A solution of 4-methyl-5-(2-aminoethyl)thiomethyl) imidazole (34.0 g.) and carbon disulphide (7.6 g.) in ethanol (250 ml.) was heated under reflux for 6 hours. Concentration followed by chromatographic purification of the product on a column of silica gel with elution by isopropyl alcohol-ethyl acetate followed by isopropyl alcohol-ethanol gave N,N'-bis-[2-(4-methyl-5-imidazolyl) methylthio)ethyl]thiourea (18 g.), m.p. 133°–135°.

(Found: C, 47.0; H, 6.1; N, 22.0%. $C_{15}H_{24}N_6S_3$ requires: C, 46.8; H, 6.3; N, 21.9%)

EXAMPLE 2

N,N'-bis-[2-((4-methyl-5-imidazolyl)methylthio)ethyl-]urea (a) A mixture of 4-methyl-5-((2-aminoethyl)thiomethyl)imidazole (8.55 g.) and 1,1-carbonyl di-imidazole (2.70 g.) was heated at 100° for 1 hour. Cooling and digesting with hot water gave a solid which was collected and washed successively with ethanol, water and methanol. Recrystallisation from methanol-ether afforded N,N'-bis-[2-((4-methyl-5-imidazolyl) methylthio)ethyl]urea, m.p. 225°–228°.

(Found: C, 48.6; H, 6.7; N, 22.8; S, 17.4%. $C_{15}N_{24}N_6OS_2$ requires: C, 48.9; H, 6.6; N, 22.8; S, 17.4%).

(b) A mixture of 4-methyl-5-((2-aminoethyl)thiomethyl)imidazole (1.6 g.) and 1,1-carbonyl di-imidazole (0.5 g.) in dimethyl formamide (12 ml.) was heated to reflux temperature whereupon the mixture solidified. After cooling, a small quanity of dimethyl formamide was added and the slurry was filtered to give the solid product which was washed with water, ethanol and ether and finally recrystallised from dimethyl formamide. Yield 0.5 g., m.p. 230°–234°.

EXAMPLE 3

N-Cyano-N',N''-bis-[2-((4-methyl-5-imidazolyl)methylthio) ethyl]guanidine (a) Lead cyanamide (8.7 g.) was added to a solution of N,N'-bis-[2-((4-methyl-5-imidazolyl)methylthio)ethyl]-thiourea in acetonitrile (100 ml.) and dimethyl formamide (20 ml.) and the resultant suspension was heated under reflux with stirring for 24 hours. Additional lead cyanamide (8.7 g.) was added and heating was continued for 24 hours. Following filtration and concentration, the residue was chromatographed on a column of silica gel, eluting with ethyl acetate-isopropyl alcohol (5:1). Recrystallisation from isopropyl alcohol-isopropyl acetate afforded N-cyano-N',N''-bis-[2-((4-methyl-5-imidazolyl) methylthio)ethyl]guanidine (0.6 g.), m.p. 92°–95°.

(b) A mixture of 4-methyl-5-((2-aminoethyl)thiomethyl)imidazole (1.71 g.) and dimethylcyanodithioimidocarbonate (0.36 g.) was heated on the steam bath for 4 hours. The addition of acetonitrile afforded the crystalline product (0.9 g.) m.p. 88°–90°.

(c) A solution of 4-methyl-5-((2-aminoethyl)thiomethyl)imidazole (6.8 g.) and dimethylcyanodiothioimidocarbonate (1.36 g.) in pyridine (6 ml.) was heated under reflux for 7 hours. Concentration, followed by trituration with acetonitrile afforded the crystalline product (2.0 g.), m.p. 93°–96°.

(d)·(i) A solution of 4-methyl-5-((2-aminoethyl)thiomethyl) imidadole (23.4 g.) in ethanol was added slowly to a solution of dimethylcyanodithioimidocarbonate (20.0 g.) in ethanol, with stirring at room temperature. The mixture was set aside overnight at room temperature. Filtration afforded N-cyano-N'-[2-((4-methyl-5-imidazolyl)methylthio) ethyl]-S-methylisothiourea (10.0 g.) m.p. 148°–150°. The filtrate was concentrated under reduced pressure and the mixture was triturated with cold water and the solid obtained, filtered off and recrystallised twice from isopropyl alcohol/ether to yield further product (27 g.), m.p. 148°–150°.

Found: C, 44.4; H, 5.6; N, 26.0; S, 24.3. $C_{10}H_{14}N_5S_2$ requires: C, 44.6; H, 5.6; N, 26.0; S, 23.8.)

(ii) A solution of silver nitrate (3.06 g.) in dimethyl formamide (20 ml.) was added to a solution of N-cyano-N'-[2-((4-methyl-5-imidazolyl)methylthio)ethyl]-S-methyl isothiourea (4.9 g.) in dimethylformamide (30 ml.). The resultant solution was kept at room temperature for 1 hour cooled and filtered to remove silver methylmercaptide, 4-methyl-5-((2-aminoethyl)thiomethyl)imidazole (3.07 g.) in dimethyl formamide (10 ml.) was added and this solution was heated overnight on the steam bath. Concentration followed by chromatographic purification of the product on a column of silica gel afforded the title compound (1.2 g.), m.p. 90°–94°, containing a small amount of water.

(Found: C, 47.4; H, 5.9; N, 27.6; S, 15.5% $C_{16}H_{24}N_8S_2$ + 3% $H_2O$ requires: C, 47.5; H, 6.3; N, 27.7; S, 15.8%)

EXAMPLE 4

N-[2-(2-Pyridylmethylthio)ethyl]-N'-[2-(4-methyl-5-imidazolyl methylthio)ethyl]thiourea dihydrochloride.

A solution prepared from S-methyl-N-[2-((4-methyl-5-imidazolyl) methylthio))ethyl]dithiocarbamate hydriodide (7.8 g.), 2-((2-aminoethyl)thiomethyl)pyridine (6.6 g.) in ethanol ((2-aminoethyl)thiomethyl)pyridine (6.6 g.) in ethanol containing sodium (0.45 g.) was heated under reflux for 20 hours. Concentration followed by chromatographic purification of the product on a column of silica gel gave the title compound, which was concentrated to a hygroscopic dihydrochloride (Found: Cl, 15.4%. $C_{16}H_{23}N_5S_3$·2 HCl requires: Cl, 15.6%)

EXAMPLE 5

N-[2-(3-Pyridylmethylthio)ethyl]-N'-[2-(4-methyl-5-imidazolylmethylthio)ethyl]thiourea The reaction of 3-((2-aminoethyl)thiomethyl)pyridine (6.6 g.) with S-methyl-N'-[2-((4-methyl-5-imidazolylmethylthio)ethyl] dithiocarbamate hydriodide (7.8 g.) by the method described in Example 4 afforded the title compound as the noncrystalline base containing a small quantity of ethyl acetate.

(Found: C, 50.2; H, 6.3; N, 17.5% $C_{16}H_{23}N_5S_3$ + 3% $CH_3COOC_2H_5$ requires: C, 50.5; H, 6.2; N, 17.8%)

EXAMPLE 6

N,N'-bis-[4-4(5)-Imidazolyl butyl]thiourea

A solution of 4-(4-aminobutyl)imidazole (5.6 g.) and carbon disulphide (1.6 g.) in ethanol (60 ml.) was kept at room temperature for 2 hours and heated under reflux for 6 hours. After concentration the residue was precipitated from ethanol with water and from ethanol with ether affording the solid product (5.3 g.) which was finally recrystallised from a large volume of acetonitrile to give the title compound, m.p. 137°–138°.

(Found: C, 56.1; H, 7.4; N, 26.1; S, 9.8% $C_{15}H_{24}N_6S$ requires: C, 56.2; H, 7.6; N, 26.2; S, 10.0%)

EXAMPLE 7

N,N'-bis-[2-(3-Bromo-2-pyridylmethylthio)ethyl]-N''-cyanoguanidine (i) A solution sodium nitrite (2.38 g.) in water (10 ml.) was added dropwise to a stirred mixture of 3-amino-2-hydroxymethylpyridine (4.8 g.) in aqueous hydrobromic acid (48%, 10 ml) and water (5 ml) at 0°–5° C. This solution of the diazonium salt was added to a hot solution of cuprous bromide (2.5 g.) in 60% hydrobromic acid and following cessation of nitrogen evolution the mixture was heated on the steam bath for 0.5 hours, diluted with water and saturated with hydrogen sulphide. Filtration, concentration to low bulk and extraction with chloroform yielded 3-bromo-2-hydroxymethyl-pyridine (4.8 g.). This was dissolved in aqueous hydrobromic acid (48%, 50 ml.), cysteamine hydrochloride (3.22 g.) added and the solution obtained was heated under reflux for 6 hours. Concentration, followed by recrystallisation from aqueous ethanol afforded 2-((2-aminoethyl)-thiomethyl)-thiomethyl)-3- bromopyridine dihydrobromide (6.1 g.), m.p. 252°–254°.

(Found: C, 23.7; H, 3.4; N, 6.7; S, 7.9. $C_8H_{11}BrN_2S.2HBr$ requires: C, 23.5; H, 3.2; N, 6.9; S, 7.8)

(ii) Reaction of dimethylcyanodithioimidocarbonate with 2-((2-aminoethyl)thiomethyl)-3-bromopyridine by the procedure described in Example 3 (d) gave N-cyano-N'-[2-((3-bromo-2-pyridyl)methylthio)ethyl]-S-methylisothiourea and a mixture of this compound (1.4 g.) and 3-bromo-2-((2-aminoethyl)thiomethyl)pyridine (2.0 g.) was heated at 140° for 6 hours. The product crystallised upon treatment with isopropyl acetate and was recrystallised from aqueous isopropanol to give the title compound (1.1 g.), m.p. 118°–119°.

(Found: C, 40.0; H, 3.8; N, 15.9; Br, 29.5; S, 11.9% $C_{18}H_{20}N_6Br_2S_2$ requires: C, 39.7; H, 3.7; N, 15.4; Br, 29.4; S, 11.8%)

EXAMPLE 8

N,N'-bis-[2-(2-Pyridylmethylthio)ethyl]-N''-cyanoguanidine (i) The reaction of 2-(2-aminoethyl)thiomethyl)pyridine with dimethylcyanodithioimidocarbonate by a method similar to that described in Example (3d) afforded N-cyano-N'-[2-(2-pyridylmethylthio)ethyl]-S-methylisothiourea, m.p. 85°–88°. (from isopropyl alcohol-ether)

(Found: C, 49.6; H, 5.4; N, 21.0; S, 24.0% $C_{11}H_{14}N_4S_2$ requires: C, 49.6; H, 5.3; N, 21.0; S, 24.1%)

(ii) The reaction of N-cyano-N'-[2-(2-pyridylmethylthio) ethyl]-S-methylisothiourea with 2-((2-aminoethyl)pyridine by the method described in Example 7 afforded the title compound m.p. 78°–80°.

(Found: C, 56.2; H, 5.7; N, 21.9; S, 16.5%. $C_{18}H_{22}N_6S_2$ requires: C, 55.9; H, 5.7; N, 21.7; S, 16.6%)

EXAMPLE 9

N,N'-bis-[2-(2-Thiazolylmethylthio)ethyl]-N''-cyanoguanidine

A solution of 2-(2-aminoethyl)thiomethyl)thiazole (1.74 g.) and dimethylcyanodithioimidiocarbonate (0.68 g.) in pyridine (10 ml.) was heated on the steam bath for 6 hours and at reflux temperature for 6 hours. Additional amine (0.3 g.) was added and heating was continued at reflux temperature for a further period of 6 hours. Concentration followed by chromatographic purification on a column of silica gel afforded the title compound (0.25 g.), m.p. 66°–68°.

(Found: C, 42.0; H, 4.6; N, 21.0%. $C_{14}H_{18}N_6S_4$ requires: C, 42.2; H, 4.6; N, 21.1%)

EXAMPLE 10

N,N'-bis-[2-(4-Methyl-5-imidazolyl)methylthio)ethyl] guanidine sulphate (i) A solution of N-[2-((4-methyl-5-imidazolyl)methylthio) ethyl]thiourea (2.29 g.) and methyl iodide (1.56 g.) in methanol (5 ml) was kept at room temperature for 18 hours affording S-methyl-N-[2-((4-methyl-5-imidazolyl)methylthio) ethyl]thiouronium iodide (2.3 g.), m.p. 128°–131°. The iodide was concentrated to the corresponding sulphate by ion-exchange on an ion-exchange resin (IRA 401) in the sulphate form.

(ii) A solution of the thiouronium sulphate (20.0 g.) and 4-methyl-5-((2-aminoethyl)thiomethyl)imidazole (9.2 g.) in water was heated under reflux for two hours. Concentration followed by recrystallisation from ethanol-methanol afforded the title compound (9.8 g.), m.p. 138°–139°.

(Found: C, 42.8; H, 6.2; N, 23.1; S, 18.9% $C_{15}H_{25}N_7S_2\cdot\frac{1}{2}H_2SO_4$ requires: C, 43.2; H, 6.3; N, 23.5; S, 19.2%)

EXAMPLE 11

N-[2-((4-Methyl-5-imidazolyl)methylthio)ethyl]-N'-[4-(4-imidazolyl)butyl]guanidine trihydrochloride A solution of S-methyl-N-[2-((4-methyl-5-imidazolyl)methylthio) ethyl]thiouronium sulphate (2.93 g.) and 4-(4-aminobutyl) imidazole (1.39 g.) in water (10 ml) was heated under reflux for 3 hours. Following concentration, the residue was converted to the free base with an ion-exchange resin (IRA 401) in the OH-form and then applied to a weakly acidic cation exchange resin (C 6 50) in the H+form and eluted with dilute hydrochloric acid. The eluate was concentrated and the residue crystallised with ethanol-ether to yield the title compound (1.9 g.) m.p. 170°–172°.

(Found: S, 23.8%. $C_{15}H_{25}N_7S . 3HCl$ requires = S, 23.9%)

EXAMPLE 12

N,N'-bis-[2-(2-Thiazolylmethylthio)ethyl]guanidine trihydrochloride

A solution of 2-((2-aminoethyl)thiomethyl)thiazole (from the dihydrobromide, 5.0 g.) and N-benzoyl-bis-dimethylthio imidocarbonate (1.7 g.) in pyridine (10 ml.) was heated at 100° for 6 hours. Following concentration, the residue was extracted with ether and the ether-extract concentrated to an oil which was chromatographed on a column of silica gel. Elution by ethyl acetate afforded N-benzoyl-N',N''-bis-[2-((2-thiazolyl)-methylthio)ethyl]guanidine (1.8 g.). This was hydrolysed with hydrochloric acid at steam bath temperature for 10 hours and concentrated. The residue was extracted with ether and recrystallised from ethanol-methanol-ether to give the title compound as colourless needles (1.4 g.), m.p. 176°–178°.

(Found: C, 32.1; H, 4.6; N, 14.2; Cl, 21.8%. $C_{13}H_{19}N_5S_4 . 3HCl$ requires: C, 32.3; H, 4.6; N, 14.5; Cl, 22.0%)

EXAMPLE 13

N-Benzenesulphonyl-N,N''-bis-[2-((4-methyl-5-imidazolyl)methylthio)ethyl]guanidine A mixture of 4-methyl-5-((2-aminoethyl)thiomethyl)imidazole (4.7 g.) and N-benzenesulphonyl-bis-dimethylthioimidocarbonate (3.6 g.) was heated at 140°–150° for 1 hour. The product was chromatographed on a column of silica gel with elution by ethyl acetate-ethanol (3:2) to give the product as a glass (5.5 g.) containing a small quantity of ethanol.

(Found: C, 49.6; H, 5.8; S, 18.3% $C_{21}H_{29}N_7O_2S_3$ + 1% EtOH requires: C, 49.7; H, 5.8; S, 18.7%)

EXAMPLE 14

N-Cyano-N'-[3-(4-imidazolyl)propyl]-N''-[2-((4-methyl-5-imidazolyl)methylthio)ethyl]guanidine The reaction of N-cyano-N'-[2-((4-methyl-5-imidazolyl)methylthio)ethyl]-S-methylisothiourea (3.5 g), with excess 4-(3-aminopropyl)imidazole (5.0 g) at 120°–130° afforded the title compound (1.7 g) m.p. 140°–142° (from isopropyl alcohol-ether).

(Found: C, 51.8; H, 6.5; N, 32.1; S, 9.2% $C_{15}H_{22}N_8S$ requires: C, 52.0; H, 6.4; N, 32.3; S, 9.3%)

EXAMPLE 15

N,N'-bis-[2-((4-Bromo-5-imidazolyl)methylthio)ethyl]-guanidine

The reaction of 4-bromo-5-[(2-aminoethyl)thiomethyl]-imidazole (from the dihydrobromide, 5.4 g) with N-benzoyl-bis-dimethylthioimidocarbonate (1.54 g.) in pyridine by the method described in Example 12 gave N-benzoyl-N',N''-bis-[2-((4-bromo-5-imidazolyl)methylthio)ethyl]guanidine as needles, m.p. 105°–110° (from ethanol-ether). Acid hydrolysis by the method described in Example 12 gave the title compound as an amorphous solid.

EXAMPLE 16

N,N'-bis[2-((3-bromo-2-pyridyl)methylthio)ethyl]-guanidine

The reaction of 3-bromo-2-[(2-aminoethyl)thiomethyl]pyridine with N-benzoyl-bis-dimethylthioimidocarbonate in pyridine by the method described in Example 12 yielded N-benzoyl-N',N''-bis-[2-((3-bromo-2-pyridyl)methylthio)ethyl]guanidine which, on acid hydrolysis, yielded the title compound.

EXAMPLE 17

N-Cyano-N'-[2-((4-methyl-5-imidazolyl)methylthio)ethyl]N''-[2-(2-thiazolylmethylthio)ethyl]guanidine Reaction of dimethylcyanodithioimidocarbonate with 2-[(2-aminoethyl)thiomethyl]thiazole by the method described in Example 3(d) gave N-cyano-N'-[2-(2-thiazolylmethylthio)ethyl]-S-methylisothiourea. Fusion of this compound (2.15 g) with 4-methyl-5-((2-aminoethyl)thiomethyl)imidazole (2.02 g) on the steam bath for 6 hours, followed by chromatographed purification on a column of silica gel with ethyl acetate/isopropyl alcohol (5:1) as eluant afforded the title compound.
(Found: C, 45.7; H, 5.4; N, 24.5% $C_{15}H_{21}N_7S_3$ requires: C, 45.5; H, 5.4; N, 24.8%)

EXAMPLE 18

N-Carbamoyl-N',N''-bis-[2-((4-methyl-5-imidazolyl)-methylthio)ethyl]guanidine

Treatment of N-cyano-N',N''-bis-[2-((4-methyl-5-imidazolyl)methylthio)ethyl]guanidine with ethanolic hydrogen chloride for 70 hours at room temperature, followed by basification and purification of the base on a column of silica gel with elution by ethanol followed by methanol afforded the title compound as an amorphous solid having m.p. 60°–70°.
(Found: C, 46.3; H, 6.4; N, 26.1% $C_{16}H_{26}N_8OS_2$ requires: C, 46.8; H, 6.4; N, 27.2%)

EXAMPLE 19

N,N''-bis[2-((3-chloro-2-pyridyl)methylthio)ethyl]-guanidine (i) A solution sodium nitrite (2.38 g) in water (10 ml) was added dropwise to a stirred mixture of 3-amino-2-hydroxymethylpyridine (4.8 g) in aqueous hydrochloric acid (48% 10 ml) and water (5 ml) at 0°–5° C. This solution of the diazonium salt was added to a hot solution of cuprous chloride (2.5 g) in conc. hydrochloric acid and following cessation of nitrogen evolution the mixture was heated on the steam bath for 0.5 hours, diluted with water and saturated with hydrogen sulphide. Filtration, concentration to low bulk and extraction with chloroform yielded 3-chloro-2-hydroxymethylpyridine (3.7 g), m.p. 42°–44° (from n-pentane). This was dissolved in aqueous hydrobromic acid (48% 50 ml), cysteamine hydrochloride (3.22g) added and the solution obtained was heated under reflux for 6 hours. Concentration, followed by recrystallisation from aqueous ethanol afforded 2-[(2-aminoethyl)thiomethyl]-3-chloropyridine dihydrobromide (6.0 g), m.p. 250°.

(ii) Reaction of the free base derived from the above dihydrobromide with N-benzoyl-bis-dimethylthioimidocarbonate in the procedure of Example 16 yields the title compound.

EXAMPLE 20

Reaction of S-methyl-N-[2-((4-methyl-5-imidazolyl)-methylthio)ethyl]thiouronium sulphate with 2-[(2-aminoethyl)thiomethyl]thiazole by the procedure of Example 10 (ii) yielded N-[2-((4-methyl-5-imidazolyl)-methylthio)ethyl]-N'-[2-(2-thiazolylmethylthio)ethyl]-guanidine.

When, in the above procedure, 2-[(2-aminoethyl)thiomethyl]thiazole in replaced by 3-bromo-2-[(2-aminoethyl)thiomethyl]pyridine and 2-(3-aminopropyl)-thiazole the products are, respectively N-[2-((4-methyl-5-imidazolyl)methylthio)ethyl]-N'-[2-((3-bromo-2-pyridyl)methylthio)ethyl]guanidine, m.p. 145°–147° (tripicrolonate), and N-[2-((4-methyl-5-imidazolyl)methylthio)ethyl]-N'-[3-(2-thiazolyl)propyl]guanidine, m.p. 149°–151° C. (tripicrate).

EXAMPLE 21

A mixture of 3-[(2-aminoethyl)thiomethyl]isothiazole and dimethylcyanodithioimidocarbonate was reacted according to the procedure of Example 3(b) and resulted in the production of N-cyano-N,N''-bis-[2-(3-isothiazolylmethylthio)ethyl]guanidine.

When the following compounds are reacted according to the above procedure with dimethylcyanodithioimidocarbonate
2-[(2-aminoethyl)thiomethyl]-3-methylpyridine,
4-(3-aminopropyl)imidazole,
2-(4-aminobutyl)thiazole,
3-[(2-aminoethyl)thiomethyl]isoxazole,
3-[(2-aminoethyl)thiomethyl]-1,2,4-triazole,
2-[(2-aminoethyl)thiomethyl]-5-amino-1,3,4-thiadiazole and
2-[(2-aminoethyl)thiomethyl]-3-hydroxy-pyridine,
the resulting products are respectively as follows:

N-cyano-N',N''-bis-[2-((3-methyl-2-pyridyl)methylthio)ethyl]guanidine, m.p. 135°–137° C.,
N-cyano-N',N''-bis-[3-(4-imidazolyl)propyl]guanidine, m.p. 116°–118° C.,
N-cyano-N',N''-bis-[4-(2-thiazolyl)butyl]guanidine, m.p. 59°–61° C.,
N-cyano-N',N''-bis-[2-(3-isoxazolylmethylthio)ethyl]guanidine,
N-cyano-N',N''-bis-[2-(3-1,2,4-triazolylmethylthio)ethyl]guanidine,
N-cyano-N',N''-bis-[2-((5-amino-2-1,3,4-thiadiazolyl)methylthio)ethyl]guanidine and
N-cyano-N',N''-bis-[2-((3-hydroxy-2-pyridyl)methylthio)ethyl]guanidine.

EXAMPLE 22

Reaction of 2-(3-aminopropyl)oxazole and dimethyl-cyanodithiomido-carbonate according to the procedure of Example 3(b) yielded N-cyano-N',N''-bis-[3-(2-oxazolyl)thiopropyl]guanidine.

EXAMPLE 23

When 4-[2-(2-aminoethyl)thioethyl]imidazole is reacted with dimethylcyanodithioimidocarbonate according to the procedure of Example 3(b), the resultant product is N-cyano-N',N''-bis-[2-(2-(4-imidazolyl)ethyl)thioethyl]guanidine.

EXAMPLE 24

In the procedure of Example 1(b) using as starting materials carbon disulphide and 3-[(2-aminoethyl)thiomethyl]isoxazole or 2-[(2-aminoethyl)thiomethyl]-3-hydroxy-pyridine, the products which are obtained are respectively, N,N'-bis-[2(3-isoxazolylmethylthio)ethyl]-thiourea and N,N'-bis-[2-((3-hydroxy-2-pyridyl)methylthio)ethyl]thiourea.

EXAMPLE 25

Reaction of N-benzoyl-bis-dimethylthioimidocarbonate with 3-[(2-aminoethyl)thiomethyl]isoxazole or 2-[(2-aminoethyl)thiomethyl]-3-hydroxy-pyridine and hydrolysis of the resultant benzoyl derivative according to Example 12 resulted in the production of N,N'-bis-[2-(3-isoxazolylmethylthio)ethyl]guanidine and N,N'-bis-[2-((3-hydroxy-2-pyridyl)methylthio)ethyl]guanidine respectively.

EXAMPLE 26

4-Methyl-5-[(2-aminoethyl)thiomethyl]imidazole and N-methanesulphonyl-bis-dimethylthioimidocarbonate are reacted together according to the process of Example 13 to give as the product N-methanesulphonyl-N',N''-bis-[2-((4-methyl-5-imidazolyl)methylthio)ethyl]guanidine.

| Ingredients | Amounts |
|---|---|
| N,N'-bis-[2-((4-Methyl-5-imidazolyl)methylthio)ethyl]thiourea | 150 mg. |
| Sucrose | 75 mg. |
| Starch | 25 mg. |
| Talc | 5 mg. |
| Stearic Acid | 2 mg. |

The ingredients are screened, mixed and filled into a hard gelatine capsule.

EXAMPLE 28

| Ingredients | Amounts |
|---|---|
| N,N'-bis-[2-((4-Methyl-5-imidazolyl)methylthio)ethyl]guanidine | 200 mg. |
| Lactose | 100 mg. |

The ingredients are screened, mixed and filled into a hard gelatine capsule.

EXAMPLE 29

N-[2-(4-Methyl-5-imidazolylmethylthio)ethyl]-N'-[2-(4-methyl-5-imidazolylmethylthio)propyl]guanidine-trihydrochloride (i) A solution of 4-hydroxymethyl-5-methylimidazole hydrochloride (14.8 g) and 2-mercaptopropylamine hydrochloride (12.8 g) in aqueous hydrobromic acid (48%, 100 ml) was heated under reflux for 6 hours, concentrated and recrystallised from ethanol-ether to give 4-methyl-5-[(2-aminopropyl)thiomethyl]imidazole dihydrobromide (30.0 g), m.p. 177°–178°.

(ii) A solution of N-[2-((5-methyl-4-imidazolyl)methylthio)ethyl]thiourea (2.29 g) and methyl iodide (1.56 g) in methanol (5 ml) was kept at room temperature for 18 hours affording S-methyl-N-[2-((5-methyl-4-imidazolyl)methylthio)ethyl]thiouronium iodide (2.3 g), m.p. 128°–131°. The iodide was converted into the corresponding sulphate by ion-exchange resin (IRA 401) in the sulphate form.

(iii) A solution of 4-methyl-5-[(2-aminopropyl)thiomethyl]imidazole (4.0 g., from the dihydrobromide) and S-methyl-N-[2-((4-methyl-5-imidazolyl)methylthio)ethyl]thiouronium sulphate (3.35 g) in water (25 ml) was heated under reflux for 4 hours. Concentration, followed by purification on ion-exchange resin C.G.50($H^+$), with elution by 0.02N hydrochloric acid, treatment with sodium hydroxide and picrolonic acid afforded N-[2-(4-methyl-5-imidazolylmethylthio)ethyl]-N'-[2-(4-methyl-5-imidazolylmethylthio)propyl]guanidine tripicrolonate (1.75 g, m.p. 173°–175°, from aqueous dimethylformamide).

(Found: C, 46.9; H, 4.5; N, 21.9; S, 5.1% $C_{16}H_{27}N_7S_2$ 3 $C_{10}H_8N_4O_5$ requires: C, 47.1; H, 4.4; N, 22.7; S, 5.5%)

The tripicrolonate was suspended in aqueous ethanol and treated with ion-exchange resin IRA 400 ($Cl^-$) and acidified with the hydrochloric acid to form the corresponding trihydrochloride salt.

(Found: Cl, 22.1% $C_{16}H_{27}N_7S_2$. 3 HCl requires: Cl, 21.7%)

EXAMPLE 30

N,N'-bis-[2-(4-Methyl-5-imidazolylmethylthio)propyl]-guanidine (i) A solution of 4-methyl-5-[(2-aminopropyl)thiomethyl]imidazole (from the dihydrobromide, 13.0 g) in ethanol (50 ml) was cooled to 0° and stirred during the gradual addition of benzoylimino dichloromethane (3.78 g). After addition the reaction mixture was set aside at room temperature for 2 hours and heated on the steam bath for 0.5 hours. Following addition to water and removal of insoluble material by filtration, the filtrate was adjusted to pH 9. The crude product obtained was purified by chromatography on a column of alumina followed by chromatographic purification on a column of silica gel (chloroform-methanol) to give N-benzoyl-N',N''-bis-[2-(4-methyl-5-imidazolylmethylthio)propyl]guanidine.

(ii) The benzoyl compound (3.2 g) was hydrolysed in concentrated hydrochloric acid (40 ml) at steam bath temperature for 5 hours. Following cooling, dilution with water and extraction with ether to remove benzoic acid, the product was purified as in Example 1 and concentrated to the picrolonate (1.35 g), m.p. 230° (decomp).

The picrolonate was dissolved in aqueous methanol and treated with ion-exchange resin IRA 401 ($Cl^-$) and acidified with hydrochloric acid to give N,N'-bis-[2-(4-methyl-5-imidazolylmethylthio)propyl]guanidine trihydrochloride.

The NMR spectrum of a solution in $D_2O$ recorded at 100 mHz showed the following resonances:

| | | |
|---|---|---|
| imidazole-2H | singlet δ8.60 | integral 2.0 protons calculated 2.0 protons |
| imidazole-$CH_2$— | singlet δ3.94 | integral 4.4 protons calculated 4.0 protons |

-continued

| | | |
|---|---|---|
| NH—CH₂—<br>CH₂—CH—S<br>\| | doublet δ3.39<br>multiplet δ3.04 | integral 6.6 protons<br>calculated 6.0 protons |
| imidazole-CH₃ | singlet δ2.37 | integral 6.0 protons<br>(internal standard) |
| —CH—<br>\|<br>CH₃ | doublet δ1.34 | |

EXAMPLE 31

N-[1-((4-Methyl-5-imidazolyl)methylthio)but-2-yl]-N'-[2-((4-methyl-5-imidazolyol)methylthio)ethyl]guanidine Reaction of 4-hydroxymethyl-5-methylimidazole and 1-mercapto-2-aminobutane in the procedure of Example 1(i) yields 4-methyl-5-[(2-aminobutyl)thiomethyl]imidazole and, when this is reacted with S-methyl-N'-[2-((4-methyl-5-imidazolyl)methylthio)ethyl]thiouronium sulphate in the procedure of Example 1(iii), the title compound is produced.

EXAMPLE 32

When the following compounds are substituted for 4-hydroxymethyl-5-methylimidazole in the procedure of Example 29(i):
4-hydroxymethyl-5-bromoimidazole,
2-hydroxymethyl-3-hydroxypyridine,
2-hydroxymethyl-3-chloropyridine,
2-hydroxymethylthiazole and
3-hydroxymethylisothiazole
the products are, respectively:

5-bromo-4-[(2-aminopropyl)thiomethyl]imidazole dihydrobromide,
3-hydroxy-2-[(2-aminopropyl)thiomethyl]pyridine dihydrobromide,
3-chloro-2-[(2-aminopropyl)thiomethyl]pyridine dihydrobromide,
2-[(2-aminopropyl)thiomethyl]thiazole dihydrobromide and
3-[(2-aminopropyl)thiomethyl]isothiazole dihydrobromide and when these compounds are reacted with S-methyl-N-[2-((4-methyl-5-imidazolyl)methylthio)ethyl]thiouronium sulphate in the procedure of Example 1(iii) the products are, respectively:
N-[2-((4-methyl-5-imidazolyl)methylthio)ethyl]-N'-[2-((4-bromo-5-imidazolyl)methylthio)propyl]guanidine,
N-[2-((4-methyl-5-imidazolyl)methylthio)ethyl]-N'-[2-((3-hydroxy-2-pyridyl)methylthio)propyl]guanidine,
N-[2-((4-methyl-5-imidazolyl)methylthio)ethyl]-N'-[2-((3-chloro-2-pyridyl)methylthio)propyl]guanidine,
N-[2-((4-methyl-5-imidazolyl)methylthio)ethyl]-N'-[2-((2-thiazolyl)methylthio)propyl]guanidine and
N-[2-((4-methyl-5-imidazolyl)methylthio)ethyl]-N'-[2-((3-isothiazolyl)methylthio)propyl]guanidine.

EXAMPLE 33

When the following compounds (obtained from the dihydrobromides described in Example 32) are substituted for 4-methyl-5-[(2-aminopropyl)thiomethyl]imidazole in the procedure of Example 30:

5-bromo-4-[(2-aminopropyl)thiomethyl]imidazole,
3-hydroxy-2-[(2-aminopropyl)thiomethyl]pyridine,
3-chloro-2-[(2-aminopropyl)thiomethyl]pyridine,
2-[(2-aminopropyl)thiomethyl]thiazole and
3-[(2-aminopropyl)thiomethyl]isothiazole
the products are, respectively:

N,N'-bis-[2-((4-bromo-5-imidazolyl)methylthio)propyl]guanidine,
N,N'-bis-[2-((3-hydroxy-2-pyridyl)methylthio)propyl]guanidine,
N,N'-bis-[2-((3-chloro-2-pyridyl)methylthio)propyl]guanidine,
N,N'-bis-[2-((2-thiazolyl)methylthio)propyl]guanidine and
N,N'-bis-[2-((3-isothiazolyl)methylthio)propyl]guanidine.

What we claim is:

1. A pharmaceutical composition to inhibit H-2 histamine receptors comprising a pharmaceutically acceptable oral or parenteral carrier and in an effective amount to inhibit said receptors a heterocyclic compound of the formula:

wherein $Het_1$ and $Het_2$, which may be the same or different, are thiazole or oxazole, which is optionally monosubstituted by lower alkyl having 1 to 4 carbon atoms, hydroxyl, halogen or amino; $Z_1$ and $Z_2$ are sulphur or a methylene group; $B_1$ is $(CH_2)_{n_1}$ and $B_2$ is $(CH_2)_{n_2}$ and when $Z_1$ is sulphur and $m_1$ is 1, $B_1$ may also be $CH_2CHR$, $CHRCH_2$, $CHRCH_2CH_2$, $CH_2CHRCH_2$ or $CH_2CH_2CHR$ wherein R is methyl or ethyl or when $Z_1$ and $Z_2$ are sulphur and $m_1$ and $m_2$ are 1, both $B_1$ and $B_2$ may also be

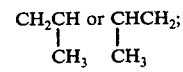

$m_1$ and $m_2$ are 0, 1 or 2 and $n_1$ and $n_2$ are 2 or 3, provided that the sum of $m_1$ and $n_1$ and the sum of $m_2$ and $n_2$ are from 2 to 4; and X is sulphur, oxygen or NY wherein Y is hydrogen, cyano, $CONH_2$ or $SO_2R_1$ wherein $R_1$ is lower alkyl or phenyl, provided that when X is NH, at least one of $Z_1$ or $Z_2$ is sulphur, or a pharmaceutically acceptable acid addition salt thereof.

2. A pharmaceutical composition of claim 1 in which the heterocyclic compound is N,N'-bis-[2-((2-thiazolyl)-methylthio)ethyl]-N"-cyanoguanidine.

3. A method of inhibiting H-2 histamine receptors which comprises administering orally or parenterally to an animal in need thereof in an effective amount to inhibit said receptors a heterocyclic compound of the formula:

wherein $Het_1$ and $Het_2$, which may be the same or different, are thiazole or oxazole, which is optionally monosubstituted by lower alkyl having 1 to 4 carbon atoms, hydroxyl, halogen or amino; $Z_1$ and $Z_2$ are sulphur or a methylene group; $B_1$ is $(CH_2)_{n_1}$ and $B_2$ is $(CH_2)_{n_2}$ and when $Z_1$ is sulphur and $m_1$ is 1, $B_1$ may also be $CH_2CHR$, $CHRCH_2$, $CHRCH_2CH_2$, $CH_2CHRCH_2$ or $CH_2CH_2CHR$ wherein R is methyl or ethyl or when $Z_1$ and $Z_2$ are sulphur and $m_1$ and $m_2$ are 1, both $B_1$ and $B_2$ may also be $$CH_2\underset{CH_3}{CH} \text{ or } \underset{CH_3}{CH}CH_2;$$

$m_1$ and $m_2$ are 0, 1 or 2 and $n_1$ and $n_2$ are 2 or 3, provided that the sum of $m_1$ and $n_1$ and the sum of $m_2$ and $n_2$ are from 2 to 4; and X is sulphur, oxygen or NY wherein Y is hydrogen, cyano, $CONH_2$ or $SO_2R_1$ wherein $R_1$ is lower alkyl or phenyl, provided that when X is NH, at least one of $Z_1$ or $Z_2$ is sulphur, or a pharmaceutically acceptable acid addition salt thereof.

4. A method of claim 3 in which the heterocyclic compound is N,N'-bis-[2-((2-thiazolyl)methylthio)ethyl]-N''-cyanoguanidine.

* * * * *

UNITED STATES PATENT AND TRADEMARK OFFICE
CERTIFICATE OF CORRECTION

PATENT NO. : 4,112,104
DATED : September 5, 1978
INVENTOR(S) : Graham John Durant and Charon Robin Ganellin It is certified that error appears in the above-identified patent and that said Letters Patent are hereby corrected as shown below:

Column 1, line 58, below the structural formula, insert
-- FORMULA I -- .

Column 3, line 6, below the structural formula, insert
-- FORMULA II -- .

Signed and Sealed this

Sixth Day of March 1979

[SEAL]

Attest:

RUTH C. MASON
Attesting Officer

DONALD W. BANNER
Commissioner of Patents and Trademarks